United States Patent
Warburton

(10) Patent No.: US 6,428,684 B1
(45) Date of Patent: Aug. 6, 2002

(54) METHOD AND APPARATUS FOR DIAGNOSING THE CONDITION OF A GAS SENSOR

(75) Inventor: P. Richard Warburton, Moon Township, PA (US)

(73) Assignee: Industrial Scientific Corporation, Oakdale, PA (US)

( * ) Notice: Subject to any disclaimer, the term of this patent is extended or adjusted under 35 U.S.C. 154(b) by 29 days.

(21) Appl. No.: 09/631,346

(22) Filed: Aug. 2, 2000

(51) Int. Cl.$^7$ ............................................. G01N 27/404
(52) U.S. Cl. .................. 205/775; 204/401; 204/406
(58) Field of Search .................. 204/401, 406; 205/775, 779.5, 781, 782.5, 786.5, 793

(56) References Cited

U.S. PATENT DOCUMENTS

| | | | | |
|---|---|---|---|---|
| 4,366,033 A | * | 12/1982 | Richter et al. | 204/406 |
| 4,498,039 A | * | 2/1985 | Galwey et al. | 204/406 |
| 5,198,771 A | * | 3/1993 | Fidler et al. | 204/406 |
| 5,202,637 A | * | 4/1993 | Jones | 204/401 |
| 5,466,356 A | * | 11/1995 | Schneider et al. | 204/406 |
| 6,248,224 B1 | * | 6/2001 | Kitzelmann | 204/431 |

OTHER PUBLICATIONS

Harris, "Quantitative Chemical Analysis" 4$^{th}$ Edition, 1995, pp. 137–138.*

* cited by examiner

Primary Examiner—Robert J. Warden, Sr.
Assistant Examiner—Kaj K. Olsen
(74) Attorney, Agent, or Firm—Dennison, Schultz & Dougherty

(57) ABSTRACT

A method and apparatus for determining the operating condition of a gas sensor apparatus including an amperometric electrochemical sensor operating normally in a potentiostat mode. By coating the sensor with a conductive coating or by varying one or more operating conditions, a response of the sensor can be determined and compared with sensor response while operating normally. This testing enables abnormalities in sensor operation to be determined, and failure of the sensor to be predicted.

10 Claims, 7 Drawing Sheets

METHOD AND APPARATUS FOR DIAGNOSING THE CONDITION OF A GAS SENSOR

BACKGROUND OF THE INVENTION

1. Field of the Invention

The present invention relates to a method and apparatus for the detection of a fault condition in a gas detecting apparatus containing one or more electrochemical gas sensors.

2. Description of Related Art

Potentially dangerous gas mixtures may be found in many work place environments. These dangers include the risk of fire or explosion from combustible gases, exposure to toxic gases and excessively high or low concentrations of oxygen.

These dangers are well known and gas detection instruments are available to detect a wide range of gases. These instruments typically contain one or more gas sensors, which give a proportional electrical response dependent upon the concentration of the gas to be detected. If the concentration exceeds allowed concentration limits, then the instrument will provide an alarm to warn nearby personnel, or it may activate other remedial actions, such as to increase the ventilation.

Gas detection instruments for safety applications are broadly divided into two groups. In the first group are portable instruments, which are designed to be hand held or worn by the user and provide personal monitoring. This group also includes transportable instruments which although not handheld, are easily moved from one location to the next. In the other group are fixed instruments, which are typically wall mounted, to provide area monitoring.

Oxygen and many of the commonly encountered toxic gases are usually detected with amperometric electrochemical gas sensors. A typical electrochemical sensor is usually constructed with two or more electrodes in contact with an electrolyte. The electrode is usually separated from the outside environment by a gas porous membrane, and other diffusion barriers. The gas to be detected enters the sensor and passes through the membrane to the working electrode, where it is either oxidized or reduced, or the rate of oxidation or reduction of the electrode or another species in electrolyte may be limited depending on the availability of the toxic gas. The resulting electrical current is proportional to the rate at which the gas is being consumed by the electrode; this type of electrochemical sensor is therefore known as an amperometric sensor. The output current is usually linearly proportional to the gas concentration, since the response is limited by the rate at which the gas to be detected can diffuse into the sensor.

The theory of operation and practical usage of electrochemical gas sensors has been discussed in detail by Chang et al (S. C. Chang, J. R. Stetter, C. S. Cha, "Amperometric Gas Sensors" *Talanta*, (1993), 40, 461) and by Hobbs et al (B. S. Hobbs, A. D. S. Tantram, R. Chan-Henry in "Techniques and Mechanisms in Gas Sensing", Ed. P. T. Mosely, J. Norris, D. E. Williams, (1991). In these sensors, the analyte gas diffuses into the sensor through a diffusion barrier to one of the electrodes, known as the working electrode. The electrons required for the oxidation or reduction of the gas flow through the external circuit to/from the counter electrode, where an equal magnitude reduction or oxidation reaction respectively occurs, and this flow of electrons constitutes an electric current, which provides the output signal. The potential of the working electrode is selected such that all the analyte gas which reaches the electrode is electrochemically oxidized or reduced. The nature of the response of the sensor to a toxic gas depends on both the design of the sensor and the nature of the gas. Some gases such as carbon monoxide (CO) and hydrogen ($H_2$) are oxidized at the electrode, whereas other gases such as chlorine ($Cl_2$), oxygen ($O_2$) and nitrogen dioxide ($NO_2$) are usually reduced in the sensor.

Oswin et al in U.S. Pat. Nos. 3,909,386, 3,992,267 and 3,824,167 describe a sensor for carbon monoxide and many variations of this basic design are known in the prior art. For most sensors, an external circuit (a potentiostat) controls the potential of the working electrode. In some sensors, such as galvanic oxygen sensors, the potential is generated by the oxidation of the counter electrode. A sensor of this latter type is known as a galvanic oxygen sensor, and descriptions have been provided by Lawson in U.S. Pat. No. 4,085,024, Tantram et al in U.S. Pat. Nos. 4,132,616 and 4,324,632, Culliname in U.S. Pat. No. 4,446,000, Bone et al in U.S. Pat. No. 4,810,352 and by Fujita et al in U.S. Pat. No. 4,495,051.

The output of most amperometric sensors is proportional to the gas concentration, and is described by the following equation:

$$I = nFCD\Delta$$

where I is the current (A), n is the number of electrons, F is the Faraday constant ($9.648 \times 10^4$ C/mol), C is the gas concentration (mol/cm$^3$), D is diffusion coefficient (cm$^2$/s) and $\Delta$ represents the cumulative diffusion barrier that the gas must pass through to reach the working electrode. In principle, it is possible to measure all the diffusion barriers comprising the sensor and thereby calculate $\Delta$, and hence calculate the sensitivity of the sensor; for example, see P. R. Warburton, M. P. Pagano, R. Hoover, M. Logman, K. Crytzer, Y. J. Warburton, *Analytical Chemistry* (1998), 70, 998. However, this calculation is not practical in common practice, and instead the gas detection instrument is calibrated by exposure to a test gas of known concentration and the output of the instrument is adjusted to match the nominal concentration of the gas. This calibration is usually performed manually and it is typically a tedious process, especially if there are a larger number of instruments. Calibration is also an expensive procedure, both in terms of the cost of the test gases with certified compositions and in terms of the labor time, and associated record keeping.

Automatic calibration methods have been described in the prior art, for example, Stetter et al in U.S. Pat. No. 4,384,925, Hyer et al in U.S. Pat. No. 4,151,738, Hartwig et al in U.S. Pat. No. 5,239,492 and Melgaard in U.S. Pat. No. 4,116,612 describe methods for automatic calibration of a gas detection instrument in which calibration gases are automatically applied to the sensors under microprocessor control. For portable instruments, so called docking stations are now available, such as the DS1000 Docking station from Industrial Scientific Corporation, Oakdale Pa. 15107, which perform the calibration and record keeping automatically.

Though most sensor technologies are very reliable, as required for a safety application, electrochemical sensors do sometimes fail in service. While most electrochemical sensors do not have a fixed service life, some sensors, such as galvanic oxygen sensors are consumed during the oxygen detection reaction and so have a limited lifetime. Whereas calibration is usually only performed at fixed time intervals, for many safety applications it is common practice to "bump test" gas detection instruments more frequently to ensure that they are working correctly. The bump test typically involves application of a test gas mixture for enough time to activate the warning alarms and/or other modes of display that indicate that the instrument responded correctly to the gas. The bump test gas procedure is commonly quicker than a calibration, but it still involves the expense of both time and test gas mixtures.

The cost and time required for manually performing calibration or bump tests on gas detection instruments have provided an incentive for the development of test methods which can be performed automatically by the instrument without human intervention. The optimum function test for a sensor is exposure of the sensor to an analyte gas of known concentration and measurement of the sensor's response. However, cost, size and complexity of the apparatus limit the ability to achieve this goal. Many simpler methods have been devised to measure the functional status of the sensor.

Electrochemical gas generators for testing gas sensors are well known in the prior art, and are described, for example, by Wolcott in U.S. Pat. No. 4,460,448 and by Rohrbacker et al in U.S. Pat. No. 5,395,501, and these generators can be applied to automated testing of sensors. Automated bump test methods have been devised in which the test gases are generated as needed, such as the electrochemical gas generators sold by Analytical Technology Inc. of Oaks, Pa. 19456 (8 Page Technical Information Sheet, titled A world of gases . . . A single transmitter) to provide test gas to automatically check the performance of gas detection instruments, and ensure that the sensors are responding within their specified limits. Finbow et al in U.S. Pat. No. 5,668,302 have incorporated an electrochemical gas generator within an electrochemical gas sensor, behind the diffusion barrier, to provide a means for automatic function testing of the gas detection instrument. Dodgson et al describe adding another electrode to an electrochemical cell to produce a test gas in PCT published application WO 98/25139. In addition, two methods for chemically generating bump test gases have been described by the Applicant in pending U.S. applications Ser. No. 08/891,235, now U.S. Pat. No. 6,098,523, and Ser. No. 09/282,661.

In another approach, Grambow et al in U.S. Pat. No. 4,321,113 calibrate the electrochemical sensors for oxidizable toxic gases such as carbon monoxide by changing the sensor potential such that oxygen is reduced at the working electrode. Since the atmospheric oxygen concentration is essentially constant and the oxygen reduction and the toxic gas oxidation currents both depend on the activity of the electrode, variations in the oxygen reduction current can be used to calibrate the sensors.

Methods have also been devised which can achieve calibration without prior knowledge of the gas concentration. One method is based on the application of Faraday's law of electrolysis to a known volume of gas, described by Tantram et al in U.S. Pat. No. 4,829,809 and by Matthiesen in U.S. Pat. No. 4,833,909. Capetanopoulos, in U.S. Pat. No. 5,741,413, and Applicant in U.S. Pat. No. 6,055,840 have designed means to measure the gas concentration and hence calibrate a sensor by changing the diffusion barrier in the gas path.

Methods have also been developed for determining if the response of a sensor to gas is limited by diffusion, or if the reaction has become rate limited by the electrode kinetics. The electrode reaction(s) may become limiting if the working electrode becomes fouled or deactivated, the counter electrode becomes deactivated or excessively polarized or for three electrode sensors if the reference electrode potential drifts. For example, Bryan et al added two external electrodes to a polarographic oxygen sensor, as described in U.S. Pat. Nos. 4,900,422 and 5,098,547, to determine if fouling had affected the output. By applying a potential to the external electrodes sufficient to electrolyze the water, oxygen gas was produced adjacent to the sensor, thus providing means to test its functional status. In addition, a small AC signal was applied between one of the external electrodes and one of the sensor internal electrodes and the impedance of the sensor diffusion membrane was measured to determine if it had become blocked.

In another example, Wang et al in U.S. Pat. No. 5,558,752 describe a method wherein the potential of the working electrode is varied with respect to the counter electrode of a two electrode polarographic sensor to determine if the output current changes with potential. If the steady state output does not change with potential, then the response is limited by diffusion and not by the electrode kinetics. Clearly, this approach can also be applied to amperometric sensors with three or more electrodes, as has been described for example by Holmström in PCT Published Application WO 99/22232. If the reference electrode potential drifts, then the electrode reaction may no longer be diffusion limited; this technique thus provides means to check for drift of the reference electrode. This method is applicable to both toxic gas sensors and oxygen sensors. Doer et al have also described electrical tests for the electrodes in HPLC electrochemical detectors in U.S. Pat. No. 5,100,530 that involve measuring the potential of the reference electrode versus the counter electrode. However, this test assumes that the counter electrode potential is steady, which may not always be a valid assumption. The reference electrode is usually designed to have a stable electrode potential, whereas stability of the counter electrode potential is not normally a design criterion for electrochemical detectors.

Other approaches to checking the functional status of electrochemical gas sensors have focused on the electrical properties of the sensor, such as the electrode capacitance. The electrodes used in many types of electrochemical gas sensors behave as though they have a large capacitance associated with them. The origin of this pseudo-capacitance is a combination of double layer capacitance and Faradaic processes occurring on the high surface electrode. The importance of electrode capacitance for electrochemical gas sensors has been discussed in more detail in P. R. Warburton, M. P. Pagano, R. Hoover, M. Logman, K. Crytzer, Y. J. Warburton, *Analytical Chemistry* (1998), 70, 998.

For a two-electrode cell, the capacitance of the whole cell is measured and it is not possible to separate the capacitive components of the working and counter electrodes. However, for a three electrode sensor, the capacitance of the working electrode can be measured independently of the counter electrode.

To a first approximation, an electrochemical sensor electrode can be modeled as a resistor and capacitor in series (RC circuit). Thus, if a potential step is applied to the sensor, there will be a current spike and subsequent current decay back to the steady state value. For a simple RC circuit, the current is described by the following equation:

$$I=(\Delta E/R)\exp(-t/RC)$$

where I is the current, $\Delta E$ is the change in potential, R is the resistance, C is the capacitance and t is the time from the potential step. In the prior art, potential step methods have been used to determine the functional status of the sensor. Jones in U.S. Pat. No. 5,202,637 applied a small voltage step to the sensor and monitored the resulting current spike. If the current spike exceeded a pre-determined limit, then the sensor was deemed to be working.

If instead of just recording the peak current on stepping the potential, the decay curve is recorded, then the electrode capacitance can be found. Capacitance C can be defined by the following equation:

$$C = \Delta Q \Delta E$$

where $\Delta Q$ is the charge passed resulting from the change in potential $\Delta E$. The charge passed is most readily found by integrating the area under the curve and since the magnitude of the potential step is known, the electrode capacitance is readily found using the above equation.

Studer has described a similar potential step method in U.S. Pat. No. 5,611,909. If the current ratio is measured at potential step ($I_{t=0}$) and again at time t later ($I_{t=t}$), then the current ratio for a simple RC circuit is given by:

$$I_{t=0}/I_{t=t} = \exp(-t/RC)$$

Studer used the ratio of the current values $I_{t=0/It=t}$ to determine the functional status of the sensor. Studer defined two parameters $C_m$ and $G_m$, which are characteristic of a sensor's functional status. By comparison of these terms with the equation for a simple RC circuit, it is apparent that $C_m$ is the electrode capacitance and $G_m$ is the electrode conductance (inverse of resistance).

Makadmini and Horn in Transducers '97, 1997 International Conference on Solid State Sensors and Actuators, Chicago, June 1997, Vol. 1, Paper 2A1.03, pp. 299 to 302, showed that the capacitance of a carbon monoxide sensor working electrode could be related to the active surface area of the electrode which in turn determined the sensitivity of that sensor. In a further development of this work, Makadmini et al in PCT Published Application WO 99/18430 varied an applied frequency to the sensor and monitored the magnitude and phase angle of the output signal. This method is a variation of electrochemical impedance spectroscopy EIS, which can be used to characterize the resistive and capacitive components of the impedance of a sensor. EIS is a very good method for measuring the status of an electrochemical sensor and diagnosing potential or actual faults, since small variations in the sensor electrodes often result in measurable changes in the EIS spectrum.

The use of electrochemical impedance techniques has also been described by Tomantschger in PCT Published Application WO 00/14523 to characterize and identify problems in potentiometric sensors used for measuring the concentrations of minor elements in molten metals.

Electrode capacitance can also be measured by cyclic voltammetry. This well known technique involves scanning the electrode potential E at a fixed scan rate (dE/dt) and measuring the current i. In the absence of an electroactive gas, the capacitance at each potential (so called differential capacitance) is given by the equation:

$$dC = i/(dE/dt)$$

This method of measuring electrode capacitance is well known in the art of electrochemistry, and details can be found in standard text books, for example "Instrumental Methods in Electrochemistry", by the Southampton Electrochemistry Group, Ellis Horwood Ltd, Chichester, 1985. Obviously, this method is readily applicable to toxic gas sensors, which typically exhibit a very large pseudo-capacitance associated with electrode redox surface processes in addition to double layer effects. For a toxic gas sensor, a small potential scan around the operating potential is preferred so as to minimize the time required for the sensor to be operable again after the test.

While certainly providing a simple and in-situ test that an instrument or controller can automatically perform on the sensor, these methods will only detect those modes of sensor failure, which affect the electrical properties of the sensor that these tests measure. For galvanic oxygen sensors, several methods have been described to predict the end of life of the sensor due to complete consumption of the anode. Tantram et al in U.S. Pat. No. 4,132,616 included a small amount of a second metal, such as copper, within the anode, which is more electropositive than the lead, but which is still sufficiently electronegative to provide the potential to the cathode for the reduction of oxygen. Once all of the lead has been consumed, the open circuit potential of the sensor will differ between lead as the active anode material and copper as the active anode material. Parker in U.S. Pat. No. 5,405,512 used multiple anodes of differing size, such that the earlier failure of the smaller anodes provided the end of life warning. Applicant has also described an electrical method that predicts the imminent failure of a galvanic oxygen sensor in U.S. application Ser. No. 09/135,058, now U.S. Pat. No. 6,096,186.

In a three-electrode sensor, the potential of the counter electrode is varied by the potentiostat circuit so as to maintain the potential difference between the working electrode and the reference electrode as a predetermined value. Further details of potentiostats can be found in standard text books on Electrochemistry, for example, the book "Electrochemistry, Calculations, Simulation and Instrumentation", edited by J. S. Mattson, H. B. Mark Jr., and H. C. MacDonald Jr.; Marcel Dekker Inc, New York 1972. The potential of the counter electrode will vary from sensor to sensor, on applying gas and in response to anything else that acts so as to change the potential difference between the working and reference electrodes. Thus, measuring the potential of the counter electrode provides a means for determining the functional state of the sensor, making it possible to diagnose such conditions as broken leads to the reference or counter electrodes, and dry-out of the sensor.

Many manufacturers of gas detection instruments incorporate a resistor, EEPROM or other electronic device on the electrochemical sensor to provide means for the instrument to confirm the presence of a sensor and to identify the sensor type. This method is used, for example, in the WorksAlone II instrument from Industrial Scientific Corporation, Oakdale, Pa. 15071.

However, this method does not detect if there is electrical continuity between the electrodes. Broken contact wires between the electrodes and the external contact is one of the failure modes encountered with electrochemical sensors. Incorporation of means to measure the electrical conductance into the gas detection circuit provides a means for checking for an open circuit condition. The conductance should be measured with an alternating current or voltage signal to avoid polarization of the electrodes. Circuits needed to measure the conductance of an electrochemical cell are well known in the art of electronics, and are generally similar to those used in conductivity meters, for example, those from YSI Inc, Yellow Springs, Ohio 45387. Conductivity has been used to detect the functional status of electrochemical gas sensors; for example, Applicant described the use of conductivity to measure the status of galvanic oxygen sensors in U.S. patent application Ser. No. 09/135,058, now U.S. Pat. No. 6,096,186. Similarly, conductivity can also be used to check the functional status of electrochemical sensors for toxic gases.

Noise signals have been used in the prior art to ascertain the status of electrochemical gas sensors. Lindsay in U.S.

Pat. No. 6,049,283 describes a method of checking the functional status of a sensor by monitoring the electrical noise produced by the sensor. If the root mean squared (rms) value of the noise is less than a predetermined threshold, the sensor is deemed to have failed. In another application, Tomantschger et al in PCT Published Application WO 00/14523 monitor the noise from an electrochemical sensor used for liquid metal analysis; if the noise levels exceed a threshold value, then the sensor is deemed to have failed.

While measuring the response of the sensor upon exposure to a known test gas is the most reliable method of ascertaining the current performance of a gas sensor, diagnostic tests offer several advantages. The prior art has shown that diagnostic tests may be able to provide a measure of the sensor function in situations where either a test gas is not available or where the test gas is available but the concentration is not known. Diagnostic tests in some cases also have the advantage that predictions of future failure of the sensor can be made while the sensor is still operational; however this approach has not been developed in the prior art. Indeed, tracking of the diagnostic results with time offers considerable potential to provide predictive capability. Furthermore, it may be advantageous to apply diagnostic tests in conjunction with the gas test to determine additional diagnostic information that is not available from either the gas test or the diagnostic tests individually.

SUMMARY OF THE INVENTION

It is therefore an object of the invention to use a modified potentiostat circuit for performing diagnostic tests on electrochemical gas sensors, allowing a gas detection instrument to perform routine tests on a sensor in addition to or in place of calibration.

It is a further object of the invention to use diagnostic tests to track the performance of a sensor and so predict the failure of the sensor in advance.

In a first embodiment of the invention, a voltmeter is included in the potentiostat circuit and is used to measure the potential difference between the reference electrode of the sensor and a metal coating on the outside surface of the sensor or on inside surfaces of the sensor that are not normally in contact with the electrolyte. In the event of an electrolyte leak, this metal coating will be contacted by the electrolyte and the metal coating will develop a redox potential. The voltmeter in the potentiostat circuit monitors the potential of the metal coating and allows a warning of an electrolyte leak.

In another embodiment of this invention, the potentiostat circuit is used to obtain the electrical time constant of the sensor by measuring the electrical noise in the sensor. The electrodes used in electrochemical gas sensors have a capacitance associated with them and the time constant acts as an RC filter to remove the higher frequencies from the noise. The frequency and amplitude distribution of the noise can be measured and the sensor time constant determined from the frequency cut off above which the noise signal is attenuated.

In another embodiment of this invention, the potentiostat circuit is used to obtain the electrical time constant of the sensor by measuring the response of the sensor to a single or double potential step waveform over a small potential range. From this test, the polarization resistance and the equilibrium potential of the working electrode are determined. Both of these parameters are indicative of changes in the electrode surface and provide markers for potential problems such as reference electrode drift or electrode poisoning.

In another embodiment of this invention, the potentiostat circuit is modified to allow the counter electrode of the sensor to be briefly disconnected from the circuit. During exposure of the sensor to the gas, the change in potential between the working electrode and the reference electrode during the period the counter electrode is disconnected is measured. From this result, the capacitance of the sensor can be determined and an analysis performed to determine whether the sensor response is limited by the rate of gas diffusion into the sensor.

In a further embodiment of this invention, a bipotentiostat is used to monitor the response current from the working and auxiliary electrodes of a sensor with four or more electrodes. If the both of the electrodes give a response proportional to the concentration of a test gas, then the ratio of the response from the working and auxiliary electrodes will be independent of the gas concentration. A change in the value of this ratio is indicative of a change in the sensor, and thus this ratio provides means for testing the functional status of a sensor.

In a still further embodiment of this invention, a potentiostat circuit is modified to allow the sensor to be tested galvanostatically. The use of small current flows through the sensor for short time periods allows the electrode capacitance to be determined. Passing larger currents through the sensor, and especially by varying the current passed with time, provides the means to characterize the electrochemical properties of the sensor. Comparison of these electrical properties with reference values or with data obtained at a different time can be used to determine the functional status of the sensor.

DESCRIPTION OF THE PREFERRED EMBODIMENTS

Figure 1:
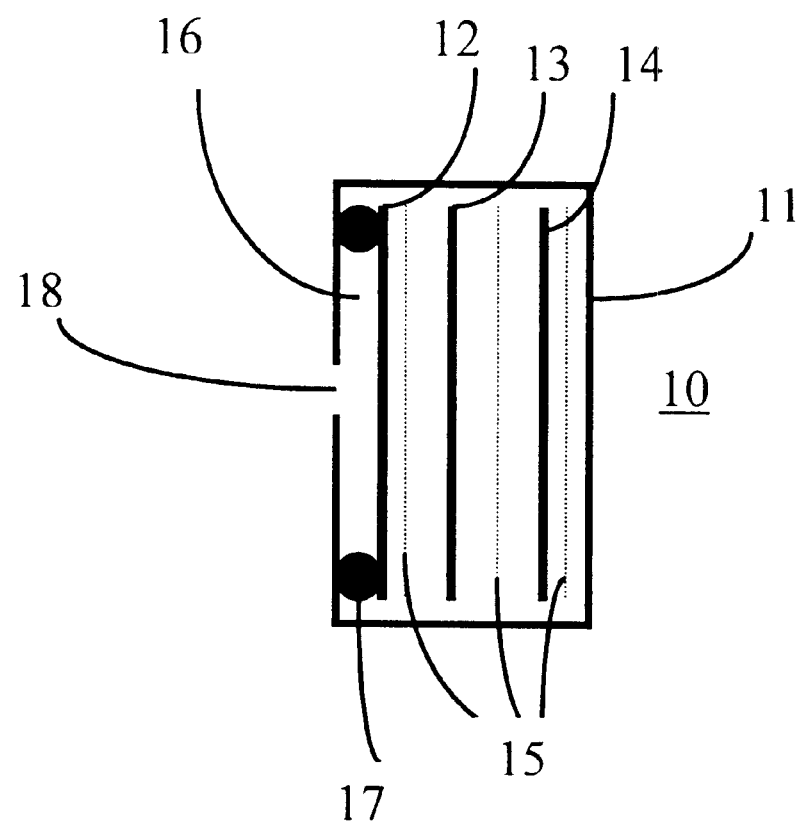
FIG. 1 is a schematic representation of a prior art electrochemical gas sensor.

A typical prior art electrochemical sensor 10 is shown in FIG. 1. The sensor comprises a sensor body 11, containing three electrodes, a working electrode 12, a reference electrode 13 and a counter electrode 14. The three electrodes 12, 13, and 14 are separated by inert media 15, soaked in electrolyte. Typically this inert media 15 is comprised of glass paper, and the electrolyte may be an aqueous or non-aqueous solution of a salt or acid, to provide ionic electrical conductivity between the electrodes 12, 13 and 14. The electrolyte is retained within the sensor 10 and is prevented from entering gas volume 16 by compression of O-ring seal 17, and the electrodes 12, 13, and 14 and the sensor housing 11.

The gas to be detected diffuses to the sensor 10 and enters gas entry hole 18 into the volume 16 within the sensor 10, then diffusing through the working electrode membrane 12. The working electrode 12 is typically comprised of a porous membrane with a precious metal (not shown) fixed onto the inner surface of the membrane.

The magnitude of the steady state response of most amperometric electrochemical gas sensors is limited by the rate at which the gas to be detected can diffuse into the sensor, and the response of this sensor is limited by the rate of gas diffusion by making the gas entry hole 18 small enough that it presents a significant diffusion barrier to the gas. The advantages of making the sensor diffusion limited are that the response is linear with concentration and the sensitivity of the sensor (sensitivity=steady state response to the gas/gas concentration) becomes independent of small variations in electrode potentials, or small losses in electrode catalytic activity.

The operation of this electrochemical sensor has been described for illustrative purposes only and many variations of electrochemical sensor design are known in the art. Further details of electrochemical sensor operation and design may be found in the references S. C. Chang, J. R. Stetter, C. S. Cha, "Amperometric Gas Sensors", Talanta (1993), 40 (4) 461–477; and B. S. Hobbs, A. D. S. Tantram, R. Chan-Henry, "Techniques and Mechanisms in Gas Sensing", Ed. P. T. Moseley, J. O. W. Norris and D. E. Williams, Adam Hilger, Bristol, 1991.

While some failure modes are common to most electrochemical gas sensors (e.g. broken contacts), many failure modes are specific to certain sensor types. For example, consumption of the anode of a galvanic oxygen sensor is specific to this type of sensor, and this failure mode is not applicable to a three-electrode carbon monoxide sensor. Conversely, a two-electrode galvanic oxygen sensor does not suffer from a drifting reference electrode, since it does not have a reference electrode. Therefore, the diagnostic tests used to identify faults will depend on the sensors used in the gas detection instrument.

One of the failure modes of electrochemical gas sensors with liquid electrolytes occurs when the electrolyte leaks out of the sensor. This may arise because of mechanical failure of the sensor housing or electrodes, damage to the sensor or flooding due to prolonged exposure to high humidity. While the use of gelled/immobilized electrolyte and solid electrolytes (e.g. Shen et al in U.S. Pat. No. 5,573,648, Schneider et al in U.S. Pat. No. 5,667,653 and Kosek et al in U.S. Pat. No. 5,527,447) offers the promise of greatly reduced leakage potential or no leakage potential, the generally better performance of the liquid electrolyte cells means that liquid electrolytes will probably continue to be used for the foreseeable future. However, the use of liquid electrolytes presents a risk of leakage, since there are many potential sites for leakage including, as applicable, the gas diffusion/electrode membrane, electrical contact wire seals, acid fill sites, etc.

Several methods for detecting the presence of electrolyte leakage have been used in the past. For example, Martell et al described in U.S. Pat. Nos. 5,744,597, 5,827,948, 5,777,208 and 5,987,965, how some sensors that use an acid electrolyte incorporate a pH paper beneath a transparent cover. In the event of a leak, there is an immediate visible indication. This approach is limited to applications where the sensor can be seen in use; in most gas detection instruments, the sensor is contained within the instrument and the sensor is not normally visible to the user. These patents also described a method of using the conductivity between two normally dry conductors to detect for leakage. In the event of an acid leak, the resultant conductivity between the two conductors is used to trigger a warning.

According to the invention, the sensor housing comprises a metal, or more preferably the housing comprises a plastic material that has been at least in part plated with a metal. This metal coating is only placed in those parts of the sensor which are normally dry and not normally in contact with the electrolyte. Suitable metals for plating include copper, nickel and chromium, though other metals may also be used. Methods for plating plastic parts are well known in the art of plastic component design and fabrication, and additional information can be obtained from standard texts such as "Standards and Guidelines for Electroplated Plastics", by the American Society of Electroplated Plastics, Prentice Hall, Englewood Cliffs, N.J., 1994. Alternatively, electrically conductive ink may be used instead of metal plating, provided the ink offers suitable redox properties as discussed below. In another embodiment, conductive plastic (e.g. carbon loaded polypropylene) has been found to perform satisfactorily in this application. However, a metal plating is the preferred embodiment and will be used as the example herein.

In the event of an electrolyte leakage, some of the electrolyte will contact the metal plating, which will thereby develop an electrochemical potential. The formation of electrochemical potentials upon contact of metal surfaces with electrolytes is well understood in the arts of electrochemistry and corrosion science (H. H. Uhlig, "Corrosion and Corrosion Control—An introduction to Corrosion Science and Engineering", $2^{nd}$ Edition, John Wiley and Sons (1971)). This electrochemical potential can be measured with respect to a suitable standard electrode, which can be an additional electrode provided for this specific purpose, or more conveniently, one of the sensor electrodes already a part of the apparatus. For a three electrode sensor, it is preferable for the sensor reference electrode be used to measure the electrochemical potential of the sensor housing, since an additional standard electrode would increase the complexity of the sensor design and the potential of the reference electrode is not affected by current flow etc. For a two-electrode sensor, either the working electrode or the counter electrode can be used to provide a standard potential. The preferred choice will depend on the sensor design. In general, the electrode whose potential varies the least during operation of the sensor is preferred for this invention.

Figure 2:
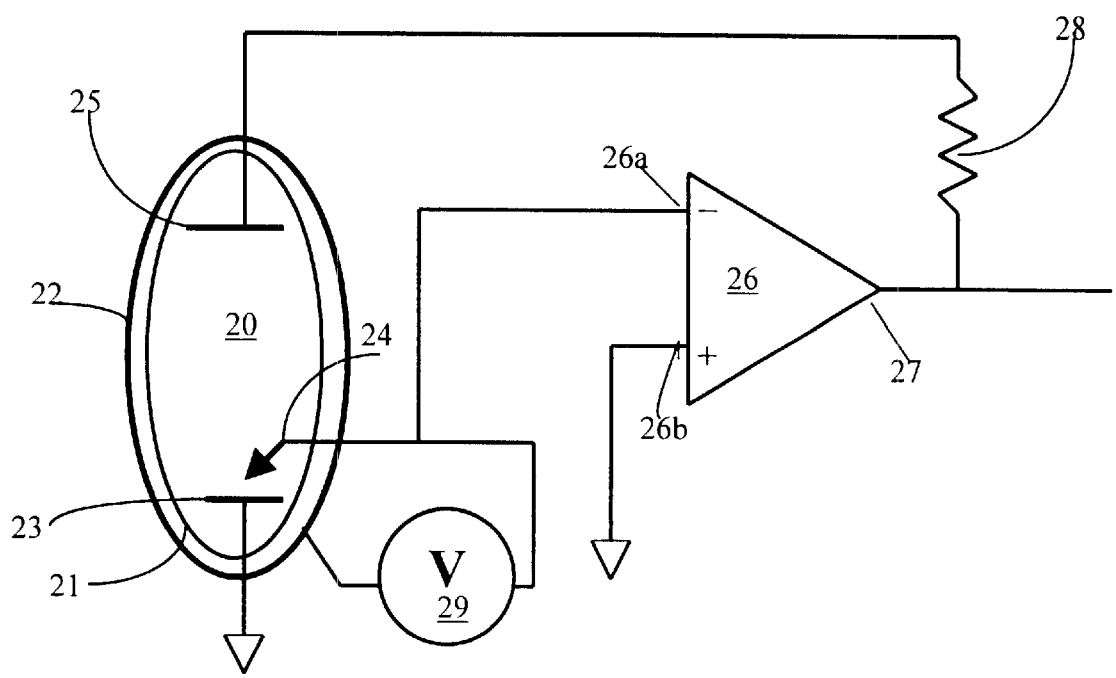
FIG. 2 is a schematic diagram of a potentiostat circuit that has been modified to provide detection of sensor electrolyte leaks.

The potential between the metal plating and the standard electrode can be measured by standard means, well know in the art of electronics. It is preferable if the circuit has a high impedance, since this will avoid polarization of the standard electrode. If the standard electrode for this invention is one of the electrodes used for normal operation of the sensor, then avoiding polarization is important, since it may otherwise potentially have a deleterious effect on the operation of the sensor. An example of a suitable circuit is shown in FIG. 2, in which sensor 20 comprises a housing 21 that has a thin, electrically conductive layer 22 on the outside. The sensor has three electrodes, a working electrode 23, a reference electrode 24 and a counter electrode 25. Sensor 20 is connected to an operational amplifier 26 that is configured to be a potentiostat; the specific potentiostat circuit shown in FIG. 2 is for illustrative purposes only and is not intended to limit the scope of this invention, many variations of potentiostat circuits being known in the art of electronics and electrochemical cells. The counter electrode 25 is connected to output 27 of an operational amplifier 26 via a feedback resistor 28. The reference electrode 24 is connected to inverting input 26a (denoted as −) of the operational amplifier 26, and both the working electrode 23 and a non-inverting input 26b (denoted as +) of the operational amplifier 26 are connected to ground. The operation amplifier 26 maintains the potential of the working electrode 23 and the reference electrode 24 at the same potential, by controlling the electrical current flow through the feedback resistor 28 and the sensor 20 via the counter electrode 25. In the event of a leak of the electrolyte (not shown) from the sensor 20, the electrolyte will contact the conductive coating 22 on the outside of the sensor housing 21, and the conductive coating will develop an electrochemical potential upon contact with the leaking electrolyte. The potential between the conductive coating 22 on the sensor housing 21 and the reference electrode 24 (which is being used as a standard electrode in this example) is measured by a voltmeter 29. If this potential exceeds a predetermined threshold, a warning is provided to the user by conventional circuitry (not shown). The voltmeter 29 represents any circuit that is capable of measuring the potential difference between the conductive coating 22 on the sensor housing 21 and the reference electrode 24. Suitable circuits are well known in the art of electronics and further details are readily available in standard texts such as "Electric Circuits" by J. W. Nilsson, Addison-Wesley publishing Company, Reading MA, 1983; or "The Art of Electronics" by P. Horowitz and W. Hill, Cambridge University Press, Cambridge, 1980. The magnitude of the potential that will be developed upon contact of the electrolyte (not shown) with the conductive coating 22 will depend on the composition of the conductive coating 22, the reference electrode 24 and the electrolyte, but typical values are from 0.1 to 1.5 V.

In another embodiment of this invention, if the RC time constant of the sensor is large, then it may control the response time of the sensor upon exposure to gas. The sensor RC time constant also acts as an RC filter, removing the higher frequencies. Any resistance in series with the working electrode, in a three electrode sensor, or either the working or counter electrodes in a two-electrode sensor, acts to increase the sensor RC time constant. Thus resistors are often used in series with amperometric gas sensors to reduce the noise of the signal. If a signal containing a broad spectrum of frequencies were applied to the sensor, then the high frequencies would be removed and the low frequencies would pass through. If the frequency distribution of the output signal were compared to the input signal, then the cut off frequency could be determined, and thus the RC constant of the sensor can be found.

One embodiment of this invention is to use the natural electrical noise of the sensor/potentiostat circuit as the source of the broadband frequency signal. The advantage of this method over the prior art is that no additional circuitry beyond what is needed for a standard potentiostat is needed. In the normal design of an electrochemical sensor circuit, additional components are present to reduce the electrical noise in the sensor circuit. It is preferred, according to the invention, that additional filtering components not be used or switched out, and instead the noise filtering is performed by software in the gas detection instrument microprocessor or other controller. Most modern gas detection instruments utilize microprocessors and many include digital filtering of the sensor signal. Means to provide digital filtering of the sensor signal can be found in standard texts, for example "Digital filters; Analysis and Design", by A. Antoniou, McGraw-Hill book Company, New York, 1979. By using the natural electronic noise of the potentiostat circuit, no additional circuit components are required to produce the test signal, and the analysis of the noise signal can also be performed by the microprocessor with software, so no additional components beyond what is required for the potentiostat are required for the analysis. For example, the potentiostat circuit in FIG. 2 can be used, though the voltmeter 29 is not needed for this embodiment of the invention. The noise is measured at the output 27 of the circuit in FIG. 2, as is the signal from a response to gas. It is advantageous if the noise signal is recorded over longer periods of time (e.g. hours), since noise tends to be random over short time periods; additionally longer periods allow for more data and so improved quality of the results.

In addition, since a noise measurement does not perturb the sensor, the test can be performed continuously during sensor operation, without detriment to the gas measurement process.

The analysis of the noise in the sensor signal is carried out by frequency analysis techniques well known in the art of electronics. These techniques are readily adapted for use with a microprocessor as commonly found in gas detection instruments. The resistance-capacitance time constant (RC time constant) of the sensor can be found from the frequency distribution of the noise. If the average frequency distribution of the noise source is known (e.g. 1/frequency is the most common) then the sensor will reduce the amplitude of those frequencies with time periods (1/f) higher than the time constant of the sensor. By determining the cutoff point above which the higher frequencies are filtered out by the sensor, the RC time constant can be found. For sensor diagnostic purposes, the RC time constant is a valuable criterion and it can be compared with previously determined thresholds for that sensor type, or it can be compared with an value established at an earlier date for the individual sensor under test, for example the value measured after a successful calibration Alternatively, the conductance/resistance can be measured by conventional means and the electrode capacitance determined from the RC time constant.

This frequency analysis process may be performed by any of the known methods for spectral analysis. However, the preferred method is to use a fast Fourier transform (FFT) of the output signal to transform the output signal from the time domain to the frequency domain and then find the cut off from the Fourier spectrum.

While it is possible to calculate the time constant of the sensor using this method, it is necessary know the noise profile being fed into the sensor. In another embodiment of the invention, the microprocessor simply monitors the amplitude—frequency profile of the sensor after the FFT analysis, and compares the profile to that of either a good sensor, or of the same sensor tested at a time when it was known to be functioning normally. A deviation in the profile from the previously recorded profile this provides the indicator that the sensor needs to be checked.

In another embodiment of the invention, a new means of measuring parameters critical to sensor performance has been developed. An electrochemical sensor in the absence of an analyte gas still has a background current. Typically, this current is small, but of great importance since the background current and the sensor noise usually determines the lower detection limit of the sensor. The fundamental reactions of the background currents in electrochemical sensors are not well understood, but they are believed to arise from the oxidation or reduction of impurities in the sensor or products from the counter electrode, oxidation or reduction of water, reduction of oxygen, or corrosion currents from the electrodes {S. C. Chang, J. R. Stetter, C. S. Cha, *Talanta* (1993), 40(4) 461}. Most electrochemical sensors are operated at zero bias, i.e. the working electrode is held at the same potential as the reference electrode. The method of the invention can be used for biased sensors, i.e. sensors whose working electrode is held at a potential different from the reference electrode, as well as for zero bias sensors.

For many amperometric sensors, it is found that there is a potential at which the background current is zero. At more positive potentials (working electrode with respect to the reference electrode), the background current increases in the positive direction (oxidation current) and at more negative potentials, the background current increases in the negative direction (reduction current). The potential at which the current is zero is an indicator of the electrode condition. If this potential changes, it is indicative of either a change in the working electrode or a change in the reference electrode. The redox processes on the surface determine the potential of a reference electrode. When the electrode is placed in contact with the electrolyte, oxidation reactions and reduction reactions will occur until equilibrium is reached. For example, on a platinum electrode, the electrode potential may be the reduction of oxygen to water and oxidation of water to oxygen, or the oxidation of platinum to platinum oxide and the reduction of this surface oxide layer back to platinum, or a mixture of both processes. The potential of the reference electrode then reflects this equilibrium. If the surface is modified in any way, for example by contamination or degradation, the electrode potential will often change. Thus, the electrode potential provides a sensitive probe of the condition of the electrode surface. The potential of the working electrode is determined similarly to the reference electrode, except the equilibrium may be modified by an externally applied potential.

The fundamental equation for electrode kinetics is the well known Butler-Volmer equation $$I=I_o[\exp(\alpha_A nF\eta/(RT))-\exp(\alpha_C nF\eta/(RT))]$$

where I is the current, $I_o$ is the exchange current density, $\alpha_A$ and $\alpha_C$ are constants known as transfer coefficients, n is the number of electrons, F is the Faraday constant ($9.648 \times 10^4$ C/mol) and $\eta$ is the overpotential, i.e. the difference between the applied potential and the equilibrium potential. Further details of electrode kinetics can be found in Electrochemistry textbooks, for example "Instrumental Methods in Electrochemistry", by the Southampton Electrochemistry Group, Ellis Horwood Ltd., Chichester, (1985). The exchange current density is usually measured by slowly scanning the potential up to half a volt positive and negative of the equilibrium circuit potential. The anodic and cathodic transfer coefficients are found from the slope of a plot of the natural logarithm of the current versus the anodic and cathodic overpotentials, respectively, and the exchange current density can be calculated from the Butler-Volmer equation. The exchange current describes the kinetics of the reaction and hence it is very sensitive to changes in the electrode surface, and provides a very good indicator for any changes in the electrode surface.

If the overpotential is small and assuming that $\alpha_C + \alpha_A = 1$, then the Butler-Volmer equation reduces to:

$$I=I_o nF/(RT)\eta$$

Thus, a plot of current versus potential for small overpotentials (<~5 mV) will be a straight line with a slope of $I_o nF/(RT)$, the slope being proportional to the exchange current density. The inverse of the slope $RT/(I_o nF)$ is known as the polarization resistance, and is used as a measure of the rate of corrosion in metallic samples, as is described in corrosion science text books, for example "Corrosion and Its Control, An Introduction to the Subject", H. Van Droffelaar and J. T. N. Atkinson, Publ. NACE International, Houston, Tex. (1995) and "Corrosion Engineering", M. G. Fontana, N. D. Greene, McGraw-Hill Book Company, New York, (1967).

While this method is known in the art of corrosion for monitoring the rate of corroding metals, it has not been applied to the study of electrochemical gas sensors. Since the exchange current density is very sensitive to changes in the surface of the electrode, the exchange current density provides a very good probe for monitoring for any changes in the working electrode surface. For example, if the electrode were poisoned, then the exchange current density would change and provide an indicator.

In the preferred embodiment of this application of the invention, either a single or a double potential step is applied to the working electrode so that the electrode is held at a small positive of the equilibrium potential and a small potential negative of the equilibrium potential of the working electrode. This potential change should be as small as possible to reduce the time required for the sensor to resume normal operation after the test, provided that the current change and potential change can be measured with sufficient accuracy. Typical values of the potential are between 1 to 5 mV. Larger values of the potential can also be used, but the sensor will require longer to recover from the test and the current—potential dependence will be less linear as the potential increases. For the purposes of illustration, a +/−5 mV potential change will be used in this discussion.

For many electrochemical sensors, the working electrode and the reference electrode are made of the same material and the two electrodes are held at the same potential. Thus, the applied potential step is +/−5 mV with respect to the reference. If the working electrode is not the same material as the reference electrode, or if the applied bias potential is not zero, the magnitude of the potential step(s) will have to determined experimentally. The potential step duration(s) should be long enough that the measured current is at steady state. A typical time is half an hour, but longer and shorter times can also be used, provided the current is essentially at steady state; the optimum time will depend on the type of sensor being tested. Some sensors with short electrical response times may only need a few seconds while other sensors with long electrical response times may need several hours.

Other means which can be used to perform this measurement are well known in the art of electrochemistry. For example, the same measurement can be performed by applying a slow potential ramp from +5 mV to −5 mV, with the ramp speed sufficiently slow that the current is at essentially steady state. For this description, +/−5 mV has been used. Clearly, other potential limits can be used; however the use of much larger potentials will result in the current potential curve no longer being as linear. In such a case, either a more complex analysis will be needed, or a less accurate test will result.

Provided the equilibrium potential is greater than −5 mV and less +5 mV of the expected value, then the current at −5 mV will be negative (reduction current) and the current at +5 mV will be positive (oxidation current). If the two currents are of the same sign, then the equilibrium potential has moved from the expected value. From the two current values, the slope of the current can be calculated.

$$\text{Slope} = (I_{+5\ mV} - I_{-5\ mV})/10\ mV$$

where $I_{+5\ mV}$ is the current at +5 mV and $I_{-5\ mV}$ is the current at −5 mV. This slope is inversely proportional to the exchange current density $I_o$ and it provides a valuable parameter for monitoring changes in the electrode surface. Since the current—potential relationship is linear over this small potential range around the equilibrium potential, the equilibrium potential (current=zero) can be calculated from the slope and the two current values at +/−5 mV.

The equilibrium potential provides a valuable parameter for monitoring for changes in either the working or reference electrode surfaces. For example, if the reference electrode potential drifts, then the measured equilibrium potential will change. The preferred means of use is to track the slope and the equilibrium potential with time. If there is a sudden change in either of these parameters, or if either of these parameters is found to be outside predetermined limits, then the user can be notified to check the calibration of the instrument, since the sensor has changed from its previous condition.

Figure 3:
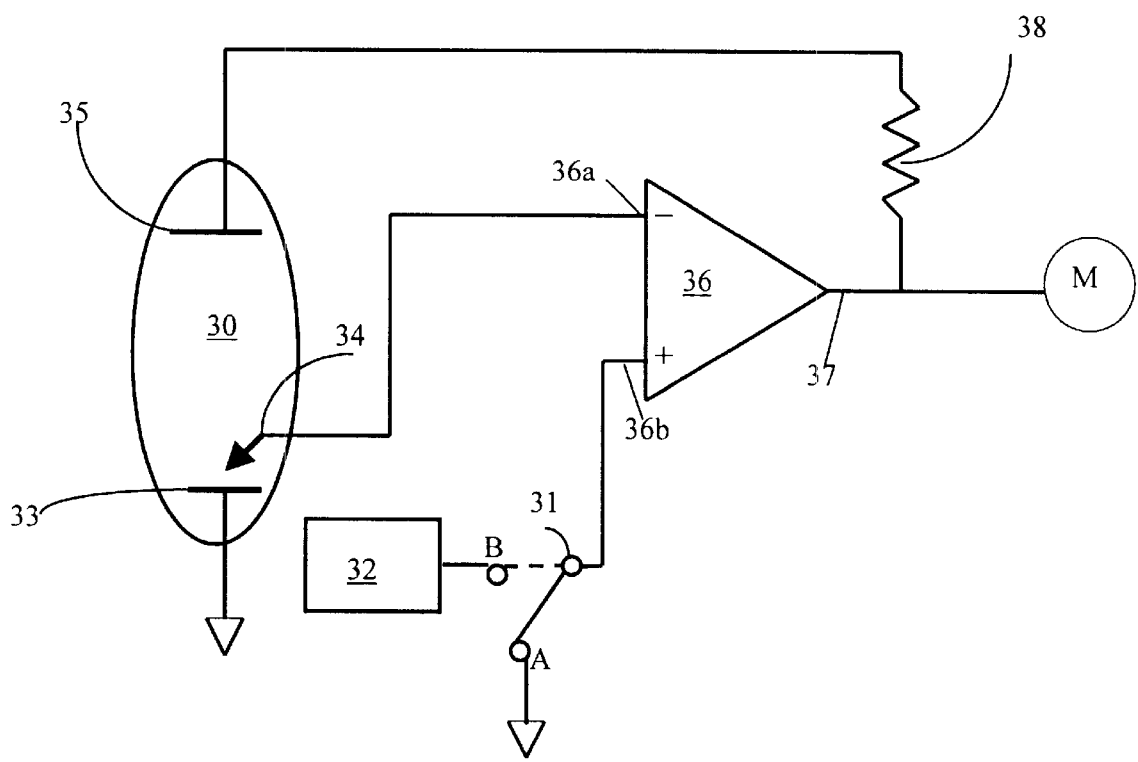
FIG. 3 is a schematic diagram of a potentiostat circuit that has been modified to provide means for applying a double potential step.

The circuit shown in FIG. 3 is a potentiostat circuit modified to apply the double potential step. The sensor 30 is connected to an operational amplifier 36. The counter electrode 35 is connected to the output 37 of the operational amplifier 36 via a feedback resistor 38. The reference electrode 34 is connected to the inverting input 36a (denoted as −) of the operational amplifier 36, and the working electrode 33 is connected to ground. The non-inverting input 36b (denoted +) of the operational amplifier 36 is connected to a switch 31. When switch 31 is in the A position, then the non-inverting input of operational amplifier 36 is connected to ground. When switch 31 is in the B position, then the non-inverting input of operational amplifier 36 is connected to a potential generator 32. In normal operation of the sensor, the switch 31 will be in the A position. In order to test the sensor 30, the switch 31 will be changed to the B position, and the potential difference between the reference electrode 34 and the working electrode 33 is increased to the new potential from potential generator 32. The operational amplifier 36 maintains the potential of the working electrode 33 and the reference electrode 34 at the potential of the non-inverting input of operational amplifier 36 from potential generator 32, by controlling the electrical current flow through the feedback resistor 38, and the sensor 30 via the counter electrode 35.

At the end of the test, switch 31 is changed back to the A position, and thus the working electrode 33 and the reference electrode 34 are again held at the same potential by operational amplifier 36.

The potential generator 32 can be a circuit that supplies the two potentials needed for this test. The test could be performed with only one potential and the standard operating potential, but the use of two potentials in addition to the operating potential is the preferred configuration. The use of two potentials provides an advantage, in providing three data points, and thus the assumption of a linear current-potential relationship can be verified. The potential generator 32 could be a potential divider with multiple taps, but a digital potentiometer is the preferred component for potential generator 32. Many circuits are known that can provide the function of the signal generator 32 to those experienced in the art of electronics. The control of potential generator 32 is readily accomplished by means of a microprocessor (not shown), as is well known to those people experienced in the art of electronics.

In another embodiment of this invention, if there is a current flowing through the sensor, then the capacitance can easily be measured by interrupting the current flow and measuring the change in the open circuit potential between the working electrode and reference electrode. This current may be from the response of the sensor to a gas, or alternatively, if the sensor has a significant background current, then this background current can be used. The significance of the current is determined by how accurately the current and the resulting change in open circuit potential can be measured. If initially a three electrode sensor with the working electrode held at potential $E_o$ relative to the reference electrode has a current I flowing through the cell, the current will drop to zero if the circuit is broken. However, if the potential of the working electrode is measured with time relative to the reference electrode, it will be found to change to a new potential $E_1$ after a time=t seconds. The capacitance C of the working electrode may readily be found from the following equation:

$$C = (E_1 - E_o)/(It)$$

It is preferable for time t to be as short as possible, provided that the change in potential can be accurately measured. A shorter measurement time will provide for faster recovery of the sensor, once the circuit is restored and the working electrode potential is again held at $E_o$. The optimum time will depend therefore on the measuring circuit, the sensor characteristics and current flow. One of the advantages of this method is that the circuit needed is relatively simple and requires only a minor modification from a standard potentiostat circuit. An example of a suitable circuit is shown in FIG. 4.

Figure 4:
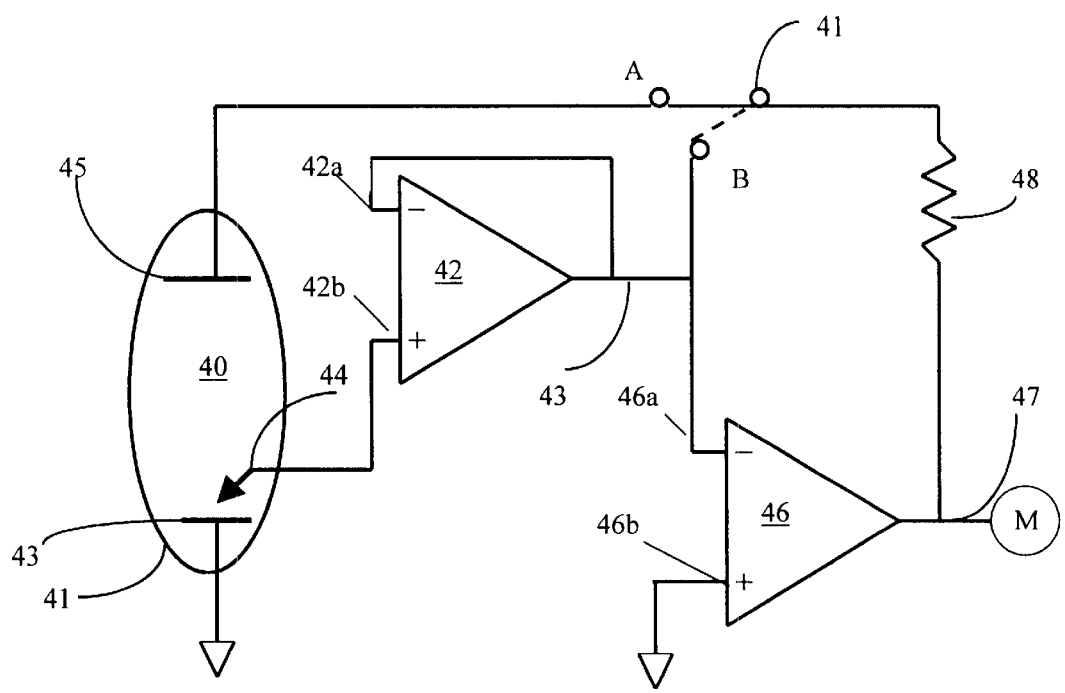
FIG. 4 is a schematic diagram of a potentiostat circuit that has been modified to measure the capacitance of an electrochemical sensor using the current interrupt test.

The circuit in FIG. 4 is a potentiostat circuit, similar in function to the circuit of FIGS. 2 and 3. The sensor 40 is connected to an operational amplifier 46, which provides the potentiostat function. When the switch 41 is in the A position, counter electrode 45 is connected to output 47 of the operational amplifier 46 via a feedback resistor 48. The working electrode 43 and the non-inverting input 46b (denoted +) of the operational amplifier 46 are connected to ground. A reference electrode 44 is connected to non-inverting input 42b of operational amplifier 42. Inverting input 42a of operational amplifier 42 is connected to output 43 of operational amplifier 42, to form an impedance buffer. When switch 41 is in the A position, the output 43 of operational amplifier 42 is connected to the inverting input 46a of operational amplifier 46, and thus the reference electrode is held at the same potential as the working electrode.

The operational amplifier 46 maintains the potential of the working electrode 43 and the reference electrode 44 at the same constant potential, by controlling the electrical current flow through the feedback resistor 48, and the sensor 40 via the counter electrode 45. For normal operation of the sensor, the switch 41 will be kept in the A position. In order to conduct the sensor diagnostic test of this embodiment of the invention, switch 41 is change to the B position. This change disconnects the counter electrode 45 from the rest of the circuit and also connects the output 43 from operational amplifier 42 to the inverting input 46b of operational amplifier 46. When switch 41 is in the B position, output 47 of operational amplifier 46 is proportional to the potential difference between the working electrode 43 and the reference electrode 44. Operational amplifier 42 acts as an impedance buffer to prevent the feedback circuit from operational amplifier 46 from driving current through the reference electrode.

The preferred method of checking the functional status of a gas sensor is to measure its response upon exposure to a test gas mixture of known composition containing some of the analyte gas. Typically, gas mixtures of known concentration require the use of gas cylinders, which are both bulky and expensive. Several methods are known for producing test gases by more convenient means, for example electrolysis or thermal decomposition; however, the concentration of gases produced by these methods is typically not known to the same accuracy as gas from a compressed gas cylinder.

Most electrochemical gas sensors are designed such that their response to the gas is limited by the rate of diffusion into the sensor. A simpler test to determine if the sensor is operating under diffusion control means would therefore be very beneficial. At steady state, the response current from an electrochemical gas sensor can be written as $$I=nFCD\Delta$$

with the terms as defined above. A diffusion-controlled current is achieved by setting the working electrode potential such that all of the analyte gas which reaches the electrode is consumed in the electrochemical reaction; thus, the concentration of the gas at the electrode surface is held at essentially zero.

The steady state flux $\phi$ of gas into the sensor is described by Fick's first law of diffusion, which can be expressed as follows:

$$\phi=CD\Delta$$

Figure 5:
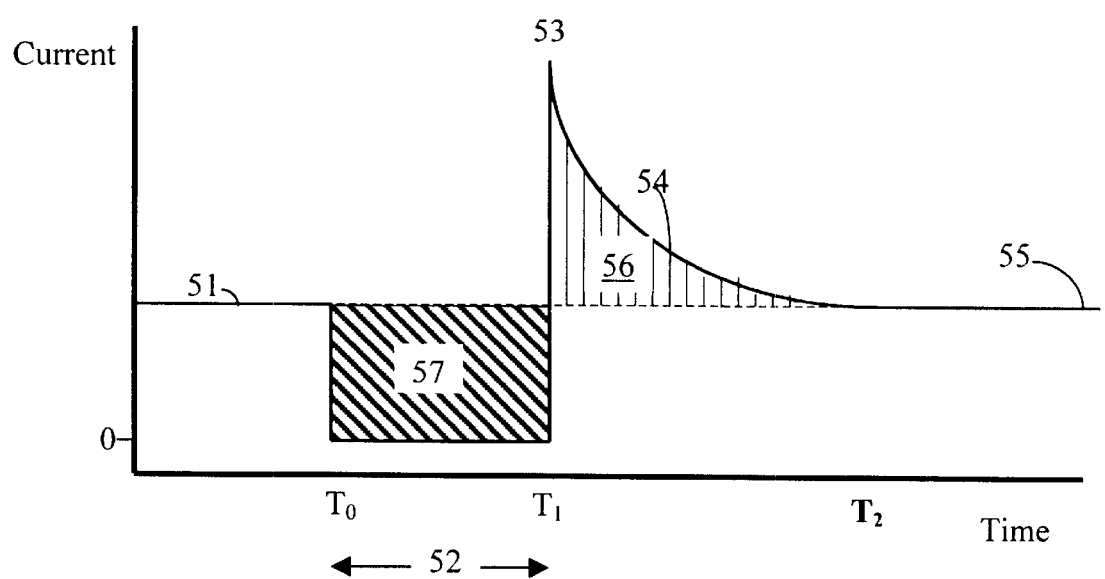
FIG. 5 is a graphical representation of a sensor output signal during a current interrupt test.

In another embodiment of this invention, the sensor circuit is momentarily broken, for example by briefly disconnecting either the working electrode or the counter electrode, while the flux of gas into the sensor continues unchanged. If the circuit is kept open for a long time, then eventually the gas concentration within the sensor will build up and the flux will decrease to zero. However, for short times, the flux of gas into the sensor is essentially constant. Upon restoring the circuit, the original current will be restored and in addition, the current corresponding to the flux of gas during the brief time when the circuit was broken will also flow as a short transient. If the sensor is truly under diffusion control, then the charge passed that corresponds to this transient should equal the steady state current in the presence of gas multiplied by the time interval the sensor circuit was kept open, as is shown in FIG. 5. This test can be performed using the same circuit as is shown in FIG. 4.

It is preferable that the current be essentially constant prior to the test, as shown by point 51 in FIG. 5. At time $T_0$, the counter electrode 45 is disconnected from the cell by changing switch 41 in FIG. 4 from position A to position B. The current flowing through the cell becomes zero at time $T_0$ when the counter electrode 45 is disconnected and the current remains zero for duration 52 of time from $T_0$ to $T_1$. At time $T_1$, the switch 41 in FIG. 4 is changed back from position B to position A and the counter electrode 45 is reconnected to the output of operational amplifier 46, via the feedback resistor 48. During the time interval from $T_0$ to $_1$, gas continued to diffuse into the sensor 40 and upon reconnecting the counter electrode 45, the concentration of gas at the working electrode 43 is higher than at steady state and so initial current 53 at time $T_1$ is higher than before the start of the test 51. As the electrode consumes the additional gas, the concentration of gas within the sensor falls back to the steady state value and so the output current decays back to the steady state again.

For many types of electrochemical gas sensor with high capacitance electrodes, a mechanistically different but functionally similar (for the user) mechanism occurs. The gas continues to react at the electrode even when the circuit is broken, resulting in a change in potential of the electrode. Upon reconnecting the sensor, the potential of the electrode is brought back to the normal operating potential. The current initially spikes and then decays back to the normal operating current of the sensor in the presence of the test gas This additional charge passed corresponds to the area N under the graph where the current exceeds the steady state value 56. This area is compared to the charge than would have passed between time $T_0$ and $T_1$ if the counter electrode 45 had not been disconnected, corresponding to area 57 in FIG. 5. The calculation of the areas 56 and 57 and the comparison are readily performed by means of a microprocessor or other controller. Thus, this test provides very simple means to determine whether a sensor is operating under diffusion control or if its output is limited by another factor.

This test will be able to identify that a problem exists because of an electrical or electrode problem. For example, if the output of the sensor is low because of reference electrode drift (three-electrode sensor), catalyst deactivation, or polarization of the counter electrode (two-electrode sensor), then this test will identify that there is a problem. However, this test will not be able to identify a sensor problem where the output current is still limited by diffusion. For example, the output of a sensor with a partially blocked diffusion barrier is still diffusion limited and this test will not be able to identify this problem.

Another embodiment of this invention can be applied to sensors with more than one working electrode. While most toxic gas sensors have three electrodes, a working electrode, reference electrode and counter electrode, additional electrodes have been added to some sensors. The most common sensor configuration to date has employed four electrodes, though more electrodes are sometimes also used. The additional auxiliary electrode(s) can be added to provide means to detect more than one gas or null out the effects of interfering gases, such as has been described by Chrzan et al in U.S. Pat. No. 5,723,036 and the models 7COSH, 4COSH and A7E/F sensors from City Technology Ltd., Portsmouth, United Kingdom. An auxiliary electrode has been used to reduce the effect of background currents in oxygen sensors (Kiesele et al in German Patent DE 19,726,453) and ammonia sensors (for example the model A7AM sensor from City Technology Ltd., Portsmouth, United Kingdom). The sensor described by Chrzan et al has working and auxiliary electrodes in the same plane. The other sensors with one or more auxiliary electrodes have the working electrode and the auxiliary electrode positioned in different planes concentrically within the sensor.

For a sensor with at least two sensing electrodes (working and auxiliary), each giving a response current ($I_1$ and $I_2$) to the analyte gas, the sensitivity S of each electrode can be calculated if the gas concentration is known.

$$S_1=I_1/(\text{Gas Concentration})$$

$$S_2=I_2/(\text{Gas Concentration})$$

Since the two sensing electrodes are exposed to the same gas, the ratio K of the signals from the two electrodes is independent of the gas concentration, provided the response of each electrode is linear with gas concentration.

$$K=I_1/I_2=S_1/S_2$$

The measured value of K can be compared against a predetermined threshold value. However, this ratio K is typically found to vary from sensor to sensor. Therefore, the preferred method is to measure the ratio $K_o$ when the sensor is first installed into a gas detection instrument, and then to compare the measured value of the ratio K at later times to this initial value $K_o$. If there is a significant change in the functional status of one of the electrodes, then the ratio K will probably change. This change in K can provide an indicator that a change has occurred, even if the sensor output meets sensitivity specifications for a working sensor.

Thus, the ratio K can be used to identify problems before these problems compromise the function of the sensor. The use of the ratio K has an additional advantage in that the sensor can be tested with a test gas of unknown concentration, since the ratio K is independent of the gas concentration, within the linear range of the sensor electrodes. Since the two sensing electrodes are behind a common diffusion barrier, changes in this common diffusion barrier, such as a partial blockage, will not result in changes in the ratio K. However, any changes in the gas diffusion barriers that are unique to a particular working or auxiliary electrode will result in a change in the ratio K. Other factors that can affect the ratio K include poor wetting of the sensing electrodes, deactivation of the catalyst, poisoning of the electrode, flooding of the electrode, etc.

This embodiment of the invention can be used with conventional four electrode sensors such as those described above. Typically, a bipotentiostat is used drive a four electrode sensor and the use and design of bipotentiostats is well known in the art of electrochemistry, and details can be found in standard texts, for example A. J. Bard, L. R. Faulkner, "Electrochemical Methods, Fundamentals and Applications", John Wiley and Sons Inc., New York 1980.

Figure 6:
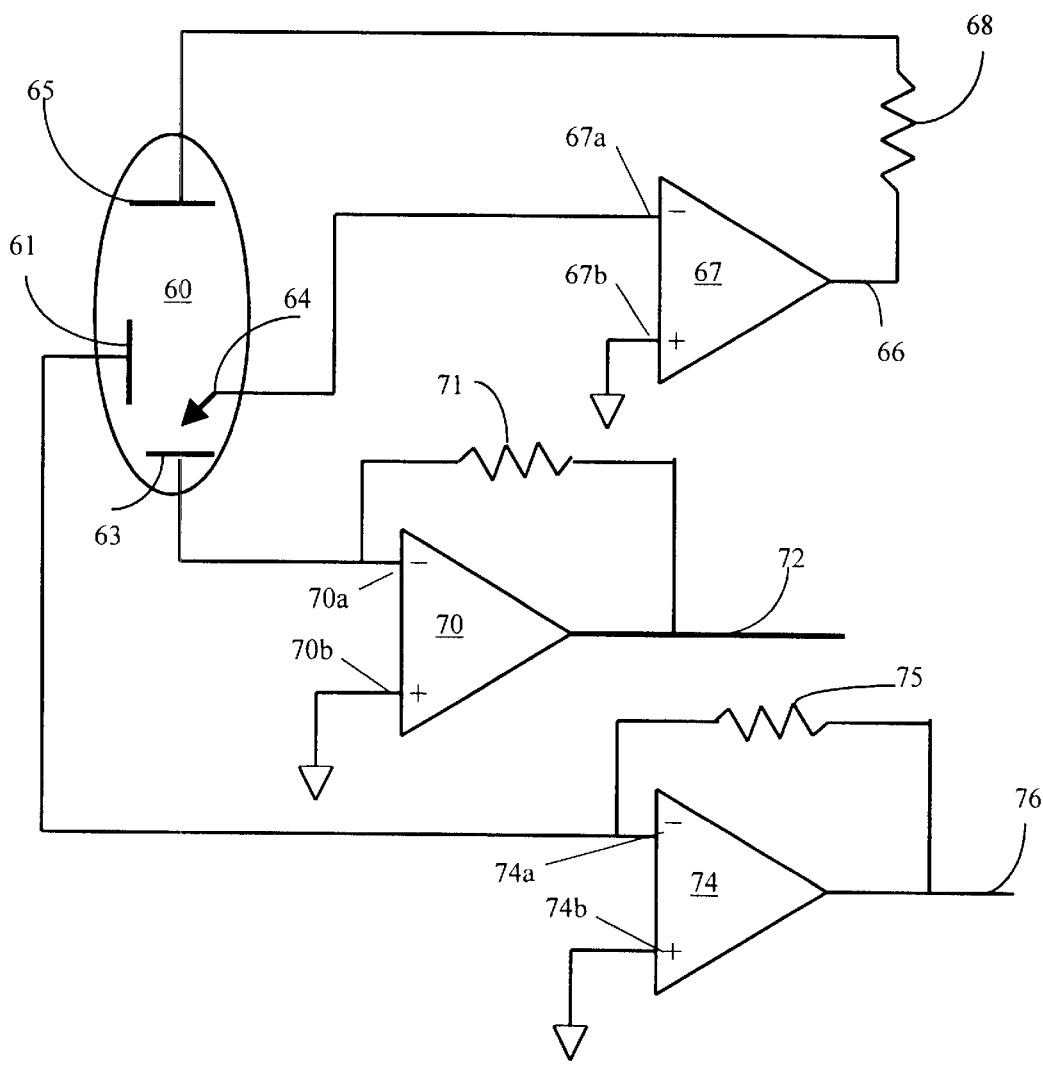
FIG. 6 is a schematic diagram of a simple bipotentiostat circuit.

An example of a bipotentiostat is shown in FIG. 6. Sensor 60 has four electrodes, a working electrode 63, a reference electrode 64, a counter electrode 65 and an auxiliary electrode 61. The counter electrode 65 is connected to output 66 of operational amplifier 67 via feedback resistor 68. Operational amplifier 67 provides the potentiostat function. The reference electrode 64 is connected to inverting input 67a (denoted −) of operational amplifier 67, and non-inverting input 67b (denoted +) of operational amplifier 67 is connected to ground. The working electrode 63 is connected to inverting input 70a of operational amplifier 70 and non-inverting input 70b is connected to ground.

Operational amplifier 70 is configured as a current follower. The inverting input 70a of operational amplifier 70 acts as a virtual ground for the working electrode 63 and the current passes through the feedback resistor 71. The voltage output 72 from operational amplifier 70 is proportional to the current flowing through the working electrode lain 63. The auxiliary electrode 61 is connected to the inverting input 74a of operational amplifier 74 and the non-inverting input 74b of operational amplifier 74 is connected to ground.

Operational amplifier 74 is also configured as a current follower. The inverting input of 74a operational amplifier 74 acts as a virtual ground for the auxiliary electrode 61 and the current passes through the feedback resistor 75. The voltage of output 76 from operational amplifier 74 is proportional to the current flowing through the auxiliary electrode 61.

The bipotentiostat shown in FIG. 6 is for a sensor in which both the working and auxiliary electrodes are operated at zero bias, i.e. at the same potential as the reference electrode. It is well known in the art of gas detection that many electrochemical sensors are operated at a non-zero bias and the circuits needed for their operation are well known to those experienced in the art of electronics. This embodiment of the invention can be used equally successfully for sensors operating at zero bias, non-zero bias and also for sensors whose working and auxiliary electrodes are operated at different biases from each other.

In the preferred embodiment of this aspect of the invention, the sensor has two or more working/auxilliary electrodes. However, if the gas detection instrument has two or more sensors that give responses that are linear with gas concentration to the same gas, then the same method can be used. Instead of the ratio K being defined as the ratio of the signals from the two electrodes, K is instead defined as the ratio of the signals from the two sensors.

In further embodiment of this invention, the capacitance of a two-electrode sensor or the working electrode capacitance of a three-electrode sensor is measured by testing the sensor in galvanostatic mode. Galvanostat circuits drive a known and controlled current through the electrochemical cell, and measure the potential across a two-electrode cell or the potential of the working electrode with respect to the reference electrode for a three-electrode cell. If the potential change $\Delta E$ between the working electrode and the reference electrode is measured in the absence of an analyte gas, for a known amount of current I passed for a known but short time t, the capacitance C can be calculated as follows:

$$C=It/\Delta E$$

The design and operation of galvanostat circuits is well known in the art, and details may be found in standard texts such as "Electrochemistry, Calculations, Simulation and Instrumentation", by J. S. Mattson, H. B. Mark Jr., and H. C. MacDonald Jr., Marcel Dekker Inc, New York 1972.

Figure 7:
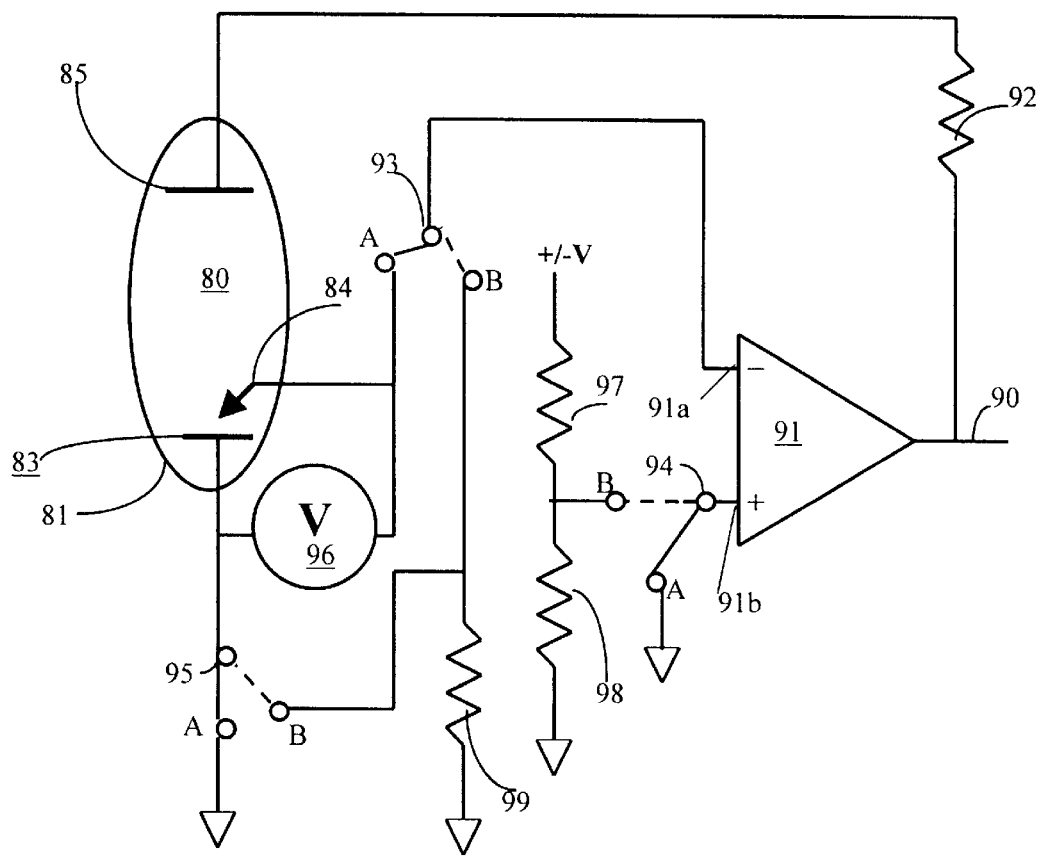
FIG. 7 is a schematic diagram of a potentiostat circuit that has been modified to perform a galvanostatic test on the sensor.

FIG. 7 shows a potentiostat circuit that has been modified to allow a galvanostatic test to be performed on the sensor. The sensor 80 is a standard configuration with a working electrode 83, reference electrode 84 and counter electrode 85. The counter electrode 85 is connected to output 90 of operational amplifier 91 via feedback resistor 92. In normal operation, switches 93, 94 and 95 are in the A positions. With these switch settings, the working electrode 83 is connected to ground, the reference electrode 84 is connected to inverting input 91a (denoted −) of operational amplifier 91 and non-inverting input 91b of operational amplifier 91 is connected to ground. In this configuration, the circuit acts as a potentiostat and keeps the working electrode 83 at the same potential as the reference electrode 84.

During the test, the switches 93, 94 and 95 are simultaneously changed to the B positions. A suitable controller (not shown) controls the switch positions within the gas detection instrument; the preferred controller is a microprocessor, but other controllers may also be used. The switches 93, 94 and 95 may be mechanical switches and any type of switch that can perform this function may be used; however, solid state switches (e.g. transistors) are preferred. In this new configuration, with switches 93, 94 and 95 in the B position, the circuit is configured as a galvanostat. The reference electrode 84 is connected to voltmeter 96 but is no longer connected to the inverting input 91a of the operational amplifier 91. The voltmeter 96 represents any circuit that is capable of measuring the potential difference between the working electrode 83 and the reference electrode 84. The non-inverting input 91b of operational amplifier 91 is now no longer connected directly to ground; instead the non-inverting input is connected to a potential divider comprising resistors 97 and 98. The potential divider (resistors 97 and 98) are connected between a voltage source (denoted +/−V), which can be either positive or negative with respect to ground, depending on whether it is desired to test the working electrode 83 as an anode or a cathode. The resistors 97 and 98 are selected to provide the desired current. The potential of the non-inverting input of operational amplifier 91 is given by the following relationship:

$$\text{Potential} = VR_{97}/(R_{97}+R_{98})$$

where V is the potential supplied at +/−V, $R_{97}$ is the resistance of resistor 97 and $R_{98}$ is the resistance of resistor 98. The operational amplifier 91 holds the potential of one end of resistor 99 at the same potential as the non-inverting input of operation amplifier 91. Since the resistor 99 is connected to ground at the other end, the current flowing through resistor 98 is:

$$\text{Current} = VR_{97}/((R_{97}+R_{98})R_{99})$$

where $R_{99}$ is the resistance of resistor 99. Thus, current can be set by changing the value of the resistors 97, 98 and 99 or the potential +/−V applied to the potential divider resistors 97 and 98.

In one embodiment of this invention, at the start of the test, switches 93, 94 and 95 are changed to the B position and a known current flows through the cell 80 between the working electrode 83 and the counter electrode 85. The potential between the working electrode 83 and the reference electrode 84 is measured by the voltmeter 96. After a short time, (typically a few seconds) the test is complete and the switches 93, 94 and 95 are returned to the A position, so that the sensor 80 can resume normal operation. The capacitance of the working electrode is calculated from the following relationship:

$$\text{Capacitance} = It/E$$

where I is the current, t is the time of the test during which the switches 93, 94 and 95 were in the B position and E is the potential measured after time t by the voltmeter 96. In this embodiment of the invention, it is preferable to keep the test time short and the current small so as to minimize the value of E to reduce the time required for the sensor 80 to recover from the test. Furthermore, since the capacitance of electrochemical sensor electrodes often varies with potential, a smaller value of E will result in an electrode capacitance more matching the capacitance of the sensor at its normal operating potential. This test is preferably performed in the absence of a test gas, but if the test is performed with a test gas present, the result needs to compensate for the current flowing through the sensor 80 from the oxidation or reduction of the test gas. The same compensation should be performed if the sensor has a significant background current under normal operating conditions.

Upon restoring the sensor to normal operation, by changing the switches 93, 94 and 95 back to the A position, there is a large current spike, which decays back to the steady state current. The height of this peak $I_p$ is given by the equation $$I_p = E/R$$

where E is the potential change from the test, as described above, and R is the resistance through the cell. This embodiment of the invention also allows measurement of the resistance across the cell. Furthermore, the area Q under the curve of the current decay from $I_p$ back to the steady state current can be used to find the electrode capacitance:

$$C = Q/E.$$

Thus, this embodiment of the invention provides a second means for measuring the electrode capacitance.

In another embodiment of this invention, which also uses the circuit in FIG. 7, a larger current is used, or more preferably, the current flowing through the sensor 80 is increased with time. For example, the current can be increased steadily with time by ramping the voltage +/−V applied to the potential divider resistors 97 and 98. The means for producing voltage ramps are well known to those experienced in the art of electronics. If a test gas is not present, then the relationship between the current flowing through the sensor 80 and the potential E measured by the voltmeter 96 is characteristic of the surface of the working electrode 83. Typically under this test, various electrochemical processes may occur including oxidation or reduction of the electrode surface, oxidation or reduction of the electrolyte or reduction of oxygen. The redox processes that occur and the current/time/potential relationships depend greatly on the type of sensor 80 and its functional status and so must be obtained empirically. Thus, comparison of the current/time/potential obtained with that of a good sensor, or with the current/time/potential obtained for the sensor 80 under test at an earlier time can be used to monitor for changes in the functional status of the sensor. Examples of the information available from this test include the active surface area of the electrode and whether the reference electrode has drifted from its initial value.

This test has the advantage of providing a very simple means for testing the status of a sensor. However, the larger potential values E measured in this embodiment (+/−0.5 to 1.0 V is typical) means that the sensor 80 will often take much longer to recover and reach its normal operating state. The time required will vary with the sensor type, and typically may vary from minutes to hours.

In another embodiment of this invention, the current through the sensor is again ramped and the potential E measured by the voltmeter 96 using the circuit in FIG. 7. In this embodiment, the test gas is applied to the sensor, and if the electrode surface capacitance is very small, then the redox process for the oxidation or reduction of the test gas may be observed directly. If the electrode capacitance is larger, the it may be necessary to run the test twice, once with the test gas and once without the test gas, and examine the difference between the two results. From the current/potential/time data, the activity of the electrode towards the oxidation or reduction of the test gas can be found. Examples of the information available from this test include identification of catalyst deactivation and poisoning of the working electrode 83 or drift of the reference electrode 84.

For testing the function of an electrochemical gas sensor, it is preferred if several tests can be implemented in concert. Each of the tests described above provided some information about the functional status of the sensor, but it is much more beneficial to have an overall fault detection scheme. The test scheme used will depend on the availability of test gas. For example, when the test gas is available with a known concentration, then the following combination of tests can be used: 1) gas test, 2) capacitance, 3) conductance, 4) background current, 5) leak test and 6) polarization resistance and equilibrium potential. Alternatively, when the test gas is available, but the concentration is not known, then the tests can be done together: 1) gas test combined with current interrupt to check if response is limited by diffusion, 2) capacitance, 3) conductance, 4) background current, 5) leak test and 6) polarization resistance and equilibrium potential.

When the sensor has both a working electrode and an auxiliary electrode, then the current ratio test has been found to be beneficial to check if the sensor electrode efficiency has changed since last verified. When a test gas is not available, the following combination of tests are found to be beneficial: 1) background current, 2) capacitance 3) conductance, 4) leak test, 5) polarization resistance and equilibrium potential.

Most modern gas detection instruments contain a microprocessor with associated memory or other means for storing data. It has been found beneficial to record the results of these diagnostic tests and to track the results with time. Each of the parameters measured can be compared against a threshold value. This threshold value can be determined by methods well known to those experienced in the art of gas detection. For example, the threshold value may be preselected by the instrument manufacturer for a given sensor type, it may be determined when the sensor is initially installed, or it may be derived from an earlier test on the sensor. If there is a sudden change in one of the parameters, then the user can be alerted.

However, it has been found to be beneficial if the rate of change of the parameters is measured as well as their absolute values. If, for example, there is a sudden change in the electrode capacitance, then even if the capacitance is within the allowed limits for a normal sensor, this sudden change may provide a predictor of future problems with the sensor. Obviously, other tests can be substituted for the ones selected above. For example, there is more than one way to measure the electrode capacitance.

The circuits described herein are examples of the implementation this invention. All circuits shown herein are for sensors that operate at zero bias (working electrode is at the same potential as the reference electrode) in normal operation, but it is simple for those experienced in the art of electronics to adapt these circuits for sensors with a non-zero bias, or to add additional components for noise reduction etc. Many variations and extensions of these circuits are known and adaptations are readily made by those experienced in the art of electronics. While the invention has been described in connection with specific embodiments thereof, it will be understood that it is capable of further modification and this application is intended to cover any variations, uses or adaptations of this invention as fall within the scope of the invention.

What is claimed is:

1. Method for testing an amperometric electrochemical sensor including a working electrode, a reference electrode, a counter electrode and an electrolyte disposed in a sensor body, a potential difference being maintained between the working electrode and the reference electrode, comprising the steps of:
    a) at a first time, increasing or decreasing the potential difference between the working electrode and the reference electrode by a predetermined amount and determining background current of the sensor after a time necessary to achieve steady state conditions;
    b) determining, at the first time, a value of potential difference between the working electrode and the reference electrode at which background current from the sensor is zero;
    c) repeating said steps a) and b) at a later time and comparing the value of potential difference at which zero current is obtained at the later time with the value of potential difference at which zero current is obtained at the first time, and
    d) determining by any change in the value of said potential difference if a change in condition of said sensor has occurred.

2. Method according to claim 1, wherein the background current is determined at both an increased potential difference and a decreased potential difference.

3. Method according to claim 2, wherein the potential difference is increased or decreased by applying a slow potential ramp from a first potential difference to a second potential difference, the value of potential difference at which background current is zero being between the first potential difference and the second potential difference.

4. Method according to claim 1, wherein the predetermined amount is about 5 mV.

5. Method for testing an amperometric electrochemical sensor including a working electrode, a reference electrode, a counter electrode and an electrolyte disposed in a sensor body, a potential difference being maintained between the working electrode and the reference electrode, comprising the steps of:
    a) at a first time, increasing or decreasing the potential difference between the working electrode and the reference electrode by a predetermined amount and determining background current of the sensor after a time necessary to achieve steady state conditions;
    b) making a plot of change in current vs. change in potential, and determining a slope of the plot;
    c) repeating said steps a) and b) at a later time, and comparing the slope obtained at the first time with the slope obtained at the later time, and
    d) determining by any change in value for said slopes if a change in condition of said sensor has occurred.

6. Method according to claim 5, wherein the background current is determined at both an increased potential difference and a decreased potential difference.

7. Method according to claim 5, wherein the predetermined amount is about 5 mv.

8. Method according to claim 5, wherein the potential difference is changed by applying a slow potential ramp from a first potential value to a second potential value, a potential at which the background current is zero being between the first potential value and second potential value.

9. A gas sensor apparatus comprising:
    an amperometric electrochemical sensor including a working electrode, a reference electrode, a counter electrode and an electrolyte disposed in a sensor body;
    a diffusion limited means for admitting a gas into the sensor body;
    a potentiostat circuit for varying potential of the counter electrode in order to maintain a potential difference between the reference electrode and the working electrode at a constant value;
    potential generating means for selectively applying at least one potential to the reference electrode with respect to the working electrode;
    a switch for testing the gas sensor apparatus by selectively connecting the potentiostat circuit between a first position in which said potentiostat circuit is connected to ground for normal operation, and a second position in which the potentiostat circuit is connected to the potential generator means; and
    means for testing the gas sensor by determining the steady state output current while the potentiostat circuit is in the second position.

10. Apparatus according to claim 9, wherein the potential generator means includes means to apply at least two potentials to the reference electrode.

* * * * *